(12) United States Patent
Bulloch et al.

(10) Patent No.: US 8,062,032 B2
(45) Date of Patent: Nov. 22, 2011

(54) APPARATUS, SYSTEM, AND METHOD FOR MAXILLO-MANDIBULAR FIXATION

(75) Inventors: Scott E. Bulloch, St. George, UT (US); Russell G. Olsen, Cedar City, UT (US)

(73) Assignee: Intrinsic Medical, LLC, Cedar City, UT (US)

( * ) Notice: Subject to any disclaimer, the term of this patent is extended or adjusted under 35 U.S.C. 154(b) by 457 days.

(21) Appl. No.: 12/257,013

(22) Filed: Oct. 23, 2008

(65) Prior Publication Data
US 2010/0105001 A1   Apr. 29, 2010

(51) Int. Cl.
*A61C 3/00* (2006.01)
(52) U.S. Cl. .......................... 433/18; 433/215
(58) Field of Classification Search ............ 433/18, 433/215, 19; 27/21.1; 606/105; 602/5, 17, 602/902; 128/848, 859–862
See application file for complete search history.

(56) References Cited

U.S. PATENT DOCUMENTS

| | | | |
|---|---|---|---|
| 1,870,566 A | 6/1931 | Heitritter | |
| 2,086,656 A * | 7/1937 | Woodward | 602/5 |
| 2,172,252 A | 4/1938 | Moore | |
| 2,502,902 A * | 4/1950 | Tofflemire | 606/54 |
| 3,675,327 A * | 7/1972 | Huget et al. | 433/215 |
| 4,230,104 A | 10/1980 | Richter | |
| 4,813,869 A | 3/1989 | Gatewood | |
| 4,834,752 A * | 5/1989 | Van Kampen | 623/13.14 |
| 4,872,449 A | 10/1989 | Beeuwkes, III | |
| 5,562,445 A | 10/1996 | Devincenzo et al. | |
| 5,613,853 A | 3/1997 | Chasan et al. | |
| 5,738,514 A | 4/1998 | Devincenzo et al. | |
| 5,842,856 A | 12/1998 | Casey | |
| 5,885,290 A | 3/1999 | Guerrero et al. | |
| 5,911,574 A | 6/1999 | Casey | |
| 6,086,365 A | 7/2000 | Fields | |
| 6,142,779 A | 11/2000 | Siegel et al. | |
| 6,260,551 B1 | 7/2001 | Sargent | |
| 7,354,270 B2 | 4/2008 | Abolfathi et al. | |
| 2002/0025502 A1 | 2/2002 | Williams | |
| 2002/0068254 A1* | 6/2002 | Campbell | 433/18 |
| 2005/0203628 A1 | 9/2005 | Elsalanty et al. | |
| 2006/0078849 A1* | 4/2006 | Parks | 433/215 |
| 2008/0046087 A1* | 2/2008 | Zucherman et al. | 623/17.16 |
| 2008/0176185 A1 | 7/2008 | Williams | |
| 2009/0024165 A1* | 1/2009 | Ferree | 606/246 |
| 2009/0036889 A1 | 2/2009 | Callender | |

FOREIGN PATENT DOCUMENTS
WO   2008048649 A2   4/2008

OTHER PUBLICATIONS
PCT/US2009/061915, International Search Report & Written Opinion, Jun. 11, 2010.

* cited by examiner

*Primary Examiner* — John J Wilson
(74) *Attorney, Agent, or Firm* — Kunzler Needham Massey & Thorpe

(57) ABSTRACT

Described herein are various embodiments of an apparatus, system, and method for maxillo-mandibular fixation. For example, according to one representative embodiment, an apparatus for maxillo-mandibular fixation includes a plurality of connectors, a fixation belt, and a release. The connectors include one or more anchors configured to attach to bone and a fixation belt attachment. The fixation belt includes a plurality of fasteners each fastener attachable to a fixation belt attachment and a flexible mesh disposed between the plurality of fasteners. The release is disposed on the fixation belt and has an engaged position restricting movement between the plurality of fasteners and a disengaged position allowing movement between the plurality of fasteners.

23 Claims, 12 Drawing Sheets

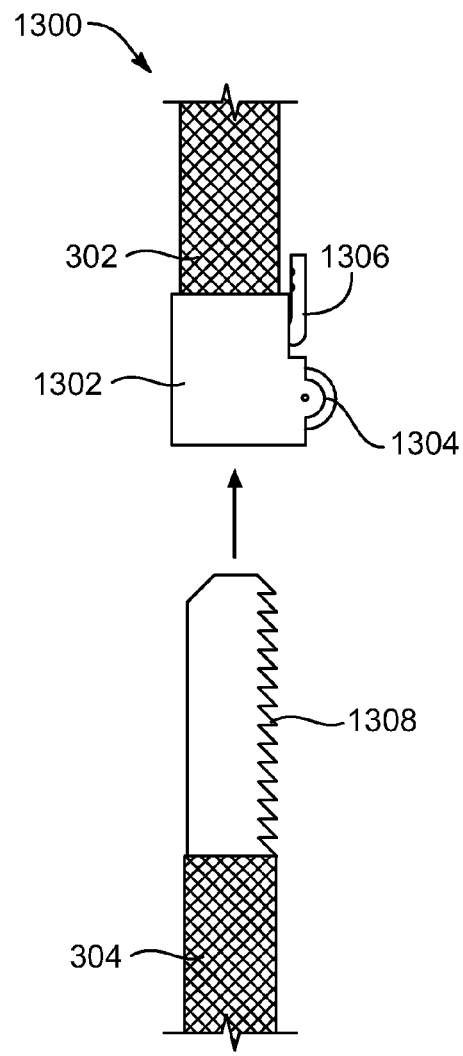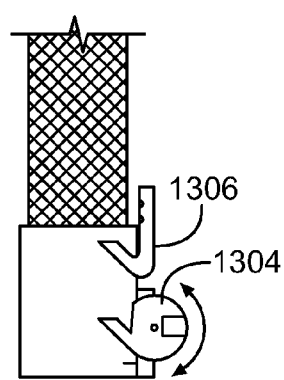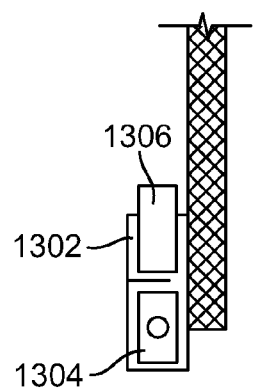
FIG. 13A
FIG. 13B
FIG. 13C

APPARATUS, SYSTEM, AND METHOD FOR MAXILLO-MANDIBULAR FIXATION

FIELD

This invention relates to oral surgery and more particularly relates to maxillo-mandibular fixation.

BACKGROUND

Often, as a result of trauma, disease, or other issues, a patient's jaws are wired together. Maxillo-mandibular fixation secures the maxilla and mandible, preventing the jaw from opening. The bones of the jaw may then heal while held into the appropriate relative location.

Typically, maxillo-mandibular fixation is carried out through the use of a fine, flexible wire. The wire is carefully wrapped around teeth in the upper and lower jaws to hold the teeth, and thus the jaw, together.

The process of wiring a jaw is difficult and time consuming, often taking an hour and a half or longer. This leads to a high cost for the process. In addition to conducting a lengthy procedure, the practitioner also faces the risk of injury and infection caused by the sharp ends of the wire during the procedure.

Often, the condition of the patient increases the difficulties. In trauma patients, it is likely that a broken jaw will be accompanied by damage to the teeth and other surrounding tissue. Consequently the practitioner must find other means of anchoring the wires, often resorting to screws inserted into bone tissue. Wire must then be strung from whatever anchor points the surgeon can find. At times, the anchors must be set at angles that lead to a likely slip of the wire off of the anchor, requiring a repeat of the wiring process.

The patient faces similar difficulties and risks, having to endure the long procedure and likely injury from sharp wires throughout the procedure and the recovery period. Once the wiring is in place, it often stretches or breaks, requiring a return to the practitioner and a repeat of the process.

Additionally, patients with wired jaws must carry wire cutters for use if the patient becomes nauseous and needs to vomit. This can be a terrifying and painful process for the patient, who must quickly cut the wires securing his or her jaw while attempting to restrain emesis. Aspiration of vomit is a likely outcome, presenting a serious danger of asphyxiation to the patient.

SUMMARY

The subject matter of the present application has been developed in response to the present state of the art, and in particular, in response to the problems and needs in the art that have not yet been fully solved by currently available maxillo-mandibular fixation devices and techniques. Accordingly, the subject matter of the present application has been developed to provide an apparatus, system, and method for maxillo-mandibular fixation that overcomes at least some shortcomings of the prior art.

According to one representative embodiment, an apparatus for maxillo-mandibular fixation includes a plurality of connectors, a fixation belt, and a release. The connectors include one or more anchors configured to attach to bone and a fixation belt attachment. The fixation belt includes a plurality of fasteners each fastener attachable to a fixation belt attachment and a flexible mesh disposed between the plurality of fasteners. The release is disposed on the fixation belt and has an engaged position restricting movement between the plurality of fasteners and a disengaged position allowing movement between the plurality of fasteners.

In some implementations of the apparatus, the flexible mesh includes a material selected from the group consisting of stainless steel, titanium, and a polymer.

According to some implementations, the flexible mesh includes two slidably connected segments. The release can be disposed at an interface between the two slidably connected segments. The engaged position of the release can restrict movement between the two slidably connected segments. The disengaged position of the release can allow movement between the two slidably connected segments. The apparatus can also include a ratchet disposed in the release. The ratchet can include a roller, gear wheel, and pawl. The roller interfaces with each of the two slidably connected segments with rotation of the roller causing relative movement between the two slidably connected segments. The gear wheel is connected to the roller. The pawl includes a spring driving the pawl against the gear wheel and an engagement surface contacting the gear wheel and restricting the rotation of the roller in one direction. The engagement surface can be removed from the gear wheel in response to the release being placed in the disengaged position.

In certain instances, the apparatus further includes a drive mechanism connected to the roller such that rotation of the drive mechanism rotates the roller. The drive mechanism can include a hex socket.

According to another embodiment, a system for maxillo-mandibular fixation includes a plurality of anchors, a plurality of connectors, a fixation belt, and a release. The plurality of anchors includes a screw configured to attach to bone and a connector attachment. The plurality of connectors includes one or more anchor attachments each attachable to a connector attachment and a fixation belt attachment. The fixation belt includes a plurality of fasteners each attachable to a fixation belt attachment and two slidably connected segments of flexible mesh disposed between the plurality of fasteners. The release is disposed on an interface between the two slidably connected segments of flexible mesh. The release is positionable in an engaged position restricting movement between the two slidably connected segments of flexible mesh and a disengaged position allowing movement between the two slidably connected segments of flexible mesh.

In certain implementations, the release includes a body and a gate. The gate is connected to the body by a hinge and is movable between the engaged position and the disengaged position. In some instances, the system includes a fingernail flange on the gate. In yet some instances, the system includes a compliant snap disposed between the gate and the body. The compliant snap releasably holds the gate in the engaged position. According to some implementations, the system includes an indicator plug with a fracture area. The indicator plug interferes with movement of the gate from the engaged position to the disengaged position. Moreover, the indicator plug allows movement of the gate from the engaged position to the disengaged position in response to a fracture of the indicator plug at the fracture area. The indicator plug can include a compliant connection with the body of the release.

The system further includes a ratchet disposed in the body of the release. The ratchet includes a roller interfacing with each of the two slidably connected segments where rotation of the roller causes relative movement between the two slidably connected segments. The ratchet also includes a gear wheel connected to the roller and a pawl having a spring driving the pawl against the gear wheel and an engagement surface contacting the gear wheel and restricting the rotation of the roller in one direction. The spring driving the pawl against the gear wheel can be released in response to the gate being in the disengaged position.

In some implementations, the gate further includes an interference surface interfering with the interface between the two slidably connected segments of flexible mesh and restricting movement between the two slidably connected segments of flexible mesh in response to the gate being in the engaged position. Further, each of the plurality of connectors can include an extension arm disposed between the one or more anchor attachments and the fixation belt attachment.

According to yet another embodiment, an apparatus for maxillo-mandibular fixation includes a plurality of connectors including one or more anchors configured to attach to bone; and a fixation belt attachment. The apparatus includes a fixation belt including a plurality of fasteners each attachable to a fixation belt attachment and two slidably connected segments of flexible mesh disposed between the plurality of fasteners. The apparatus also includes a release disposed on an interface between the two slidably connected segments of flexible mesh. The release includes an engaged position restricting movement between the two slidably connected segments of flexible mesh, and a disengaged position allowing movement between the two slidably connected segments of flexible mesh. The apparatus also includes a ratchet disposed in the release that includes a roller interfacing with each of the two slidably connected segments where rotation of the roller causes relative movement between the two slidably connected segments. The ratchet further includes a gear wheel connected to the roller and a pawl comprising a spring driving the pawl against the gear wheel and an engagement surface contacting the gear wheel and restricting the rotation of the roller in one direction.

In certain instances, the paw is freed from the gear wheel in response to the release being placed in the disengaged position.

In yet another representative embodiment, a method for maxillo-mandibular fixation of a patient includes fixing a plurality of anchors to at least one bone of the patient, coupling each of a plurality of connectors to a respective one of the plurality of anchors, coupling a respective one of at least two fixation belts to an at least one pair of opposing anchors, and tensioning each of the at least two fixation belts. In certain implementations, each of the fixation belts includes a release mechanism and the method includes actuating the release mechanism to reduce tension in the fixation belts. The method can include coupling at least one indicator plug to each of the at least two fixation belts. The indicator plugs being configured to provide a visual indication that the release mechanism has been released.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which:

FIGS. 13A and 13B are front views illustrating an alternative embodiment of a portion of a fixation belt with a front panel of a release removed in FIG. 13B and FIG. 13C is a side view illustrating the fixation belt portion shown in FIG. 13A in accordance with the present invention;

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
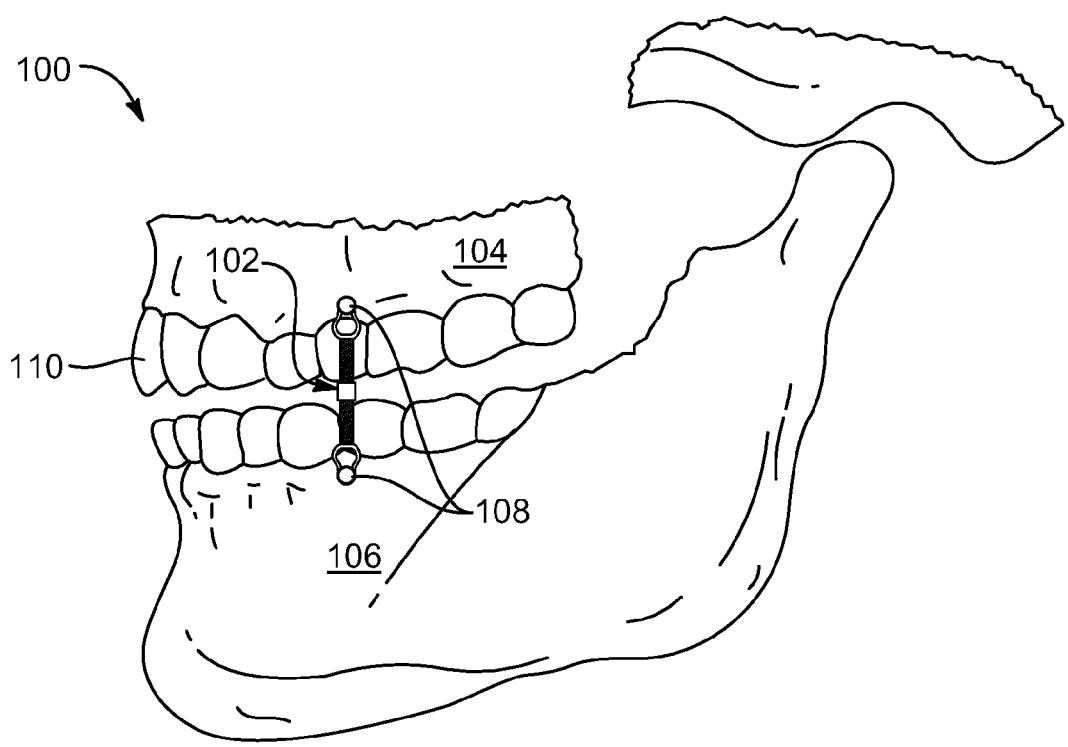
FIG. 1 is a side view illustrating one embodiment of a fixation belt connected to the maxilla and mandible in accordance with the present invention.

FIG. 1 illustrates one embodiment of a side view of an apparatus 100 for maxillo-mandibular fixation. The illustrated embodiment includes a fixation belt 102 connected to a maxilla 104 and mandible 106 using a plurality of connectors 108. The apparatus 100 for maxillo-mandibular fixation secures the maxilla 104 and the mandible 106 relative to one another.

The plurality of connectors 108 are each connected to the maxilla 104 or the mandible 106 in one embodiment. Alternatively, connectors 108 may be attached to other bones or one or more teeth 110. For example, in a patient with existing orthodontia, a connector 108 may be attached to that orthodontia and thus connected to one or more teeth. In another example, in a patient with extensive damage to the mandible, a connector 108 may be attached to the nearest stable bone.

In certain embodiments, the plurality of connectors 108 may include extensions to provide convenient attachments to bone along with accessible fixation belt attachments. Connectors 108 may be fixed to bone using anchors. Connectors 108 with extensions and anchors are further described in relation to FIG. 10.

The fixation belt 102, in one embodiment, is attachable to the plurality of connectors 108. The fixation belt 102 restricts movement of the plurality of connectors 108 relative to one another in one embodiment. Since the connectors 108 are connected to the maxilla 104 and mandible 106, other bones, or teeth, the restriction of movement between the connectors 108 fixes the jaw. In certain embodiments, the fixation belt 102 is flexible.

In an alternate embodiment, a plurality of fixation belts 102 may be employed. For example, a fixation belt 102 may be installed on each side of a patient's jaw. As will be appreciated by one skilled in the art, any number of fixation belts 102 may be employed depending on the needs and condition of the patient.

The fixation belt 102 may comprise any material having the tensile strength necessary to hold the maxilla 104 and the mandible 106 together. For example, in one embodiment, the fixation belt 102 may comprise a stainless steel mesh. In another example, the fixation belt 102 may comprise a band comprising a polymer. In yet another example, one embodiment of the fixation belt 102 may comprise one or more titanium woven wires. In another example, the fixation belt 102 may comprise a composite material, such as aramid fiber in a polymer matrix.

The fixation belt 102 may comprise elements arranged to provide the desired tensile strength. For example, the fixation belt 102 may comprise a mesh, a woven material, one or more straps, one or more bands, one or more wires, one or more filaments, one or more fibers, a combination of elements, or the like. In certain embodiments, the materials in the fixation belt 102 comprise one or more strands arranged such that the ends of the strands do not protrude from the fixation belt 102. For example, the fixation belt 102 may comprise a woven mesh of titanium wires with the ends of the wires contained within caps located at the ends of the fixation belt 102.

Beneficially, the fixation belt 102 allows for relatively easy and quick fixation of the bones of the jaw 104, 106. Additionally, the fixation belt 102 reduces the risk of injury caused by a protruding wire.

Figure 2:
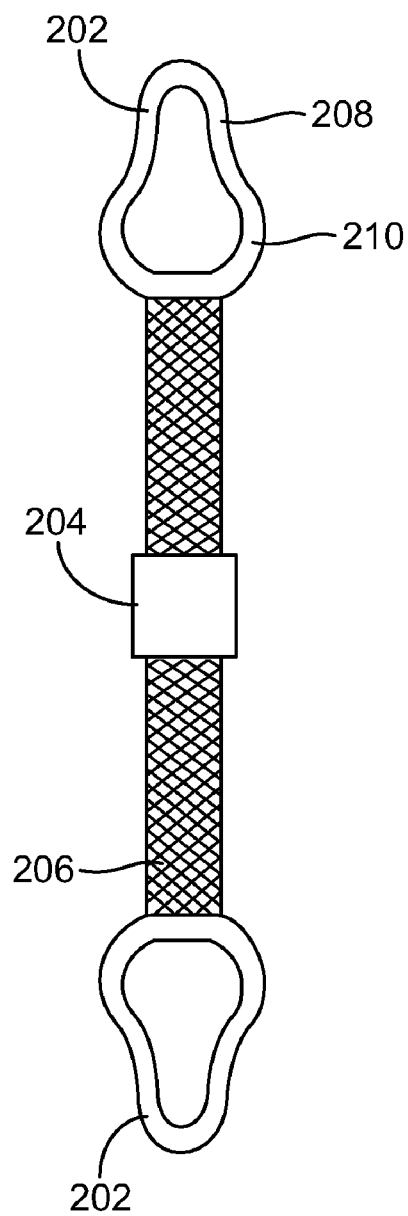
FIG. 2 is a front view further illustrating the fixation belt of FIG. 1 in accordance with the present invention.

FIG. 2 is a front view further illustrating the fixation belt 102 of FIG. 1 in accordance with the present invention. The fixation belt 102, in one embodiment, includes a plurality of fasteners 202, a release 204, and a flexible mesh 206. The fixation belt 102 restricts movement between a plurality of connectors 108.

Each of the plurality of fasteners 202, in one embodiment, is attachable to one or more connectors 108. Each of the plurality fasteners 202 may comprise any type of fastener known in the art. For example, in the illustrated embodiment, each fastener 202 is a keyhole fastener, configured to slide over a button on a connector 108 at a wide portion 210, and be secured by the button at a narrow portion 208. In the illustrated embodiment, the narrow portion 208 is located at a distal end of the fastener 202 relative to the wide portion 210, resulting in a secure connection to the connector 108 when the fixation belt 102 is under tension.

As will be appreciated by one skilled in the art, a variety of types and configurations of fastener 202 may be employed without departing from the scope and spirit of the invention. For example, in one embodiment, a fastener 202 may comprise a snap. In another embodiment, a fastener 202 may comprise a hook. In yet another embodiment, the fastener 202 may comprise a hole secured by a screw driven into bone.

In another embodiment, each of the plurality of fasteners 202 may attach to a fixation belt attachment (not shown) on a connector 108. Fixation belt attachments are further described in relation to FIG. 10.

The release 204, in one embodiment, releases the fixation belt 102 to free the connectors 108 and allow the jaw to open. The release 204 may be employed to remove the fixation belt 102 after the jaw has healed. Additionally, the release 204 may be used by the patient to free the jaw during an emergency, such as when nauseous. In one embodiment, the release is disposed on the fixation belt 102.

Various types and configurations of release 204 may be employed in the invention. In one embodiment, the release 204 releases one or more fasteners 202 from one or more connectors 108. For example, the release 204 may be a fingernail flange on a snap fastener 202 that may be pried off with a fingernail.

In the illustrated embodiment, the release 204 comprises a mechanism that allows the fixation belt 102 to extend when the release 204 is disengaged. Some embodiments of releases 204 that allow the fixation belt 102 to extend when disengaged are described in greater detail in relation to FIGS. 3-9.

In the illustrated embodiment of the fixation belt 102, the plurality of fasteners 202 are connected by a flexible mesh 206 disposed between the plurality of fasteners 202. The flexible mesh 206 may comprise any material with the tensile strength required to fix the maxilla and the mandible. Such materials include, but are not limited to, titanium, stainless steel, polymers such as nylon or aramid, or the like.

The flexible mesh 206, in one embodiment, has a relatively low amount of elastic or plastic deformation along its length under the stress generated by installation and use of the fixation belt 102. In an alternate embodiment, the flexible mesh 206 undergoes a degree of elastic deformation along its length during installation of the fixation belt 102 such that the fixation belt 102 is under tension when the jaw is fully closed.

Figure 3:
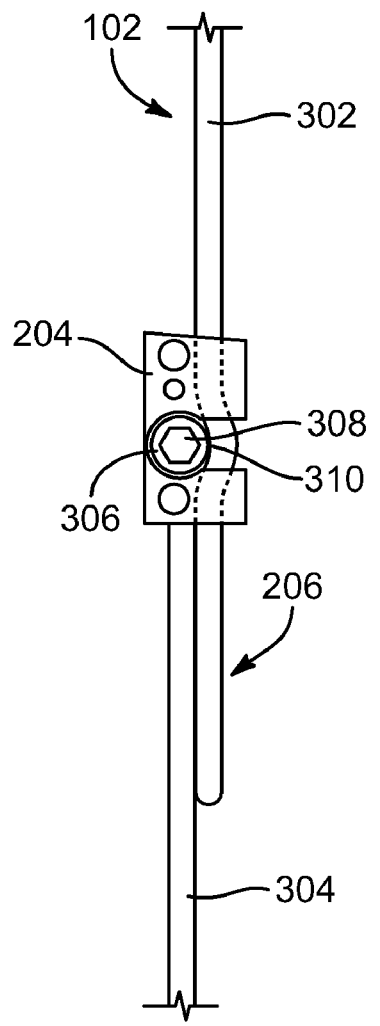
FIG. 3 is a side view further illustrating the fixation belt of FIG. 1 in accordance with the present invention.

FIG. 3 is a side view further illustrating a portion of one embodiment of a fixation belt 102 in accordance with the present invention. The fixation belt 102, in one embodiment, includes two slidably connected segments 302, 304 of flexible mesh 206, a release 204, a roller 306, and a drive mechanism 308. The fixation belt 102 in the illustrated embodiment is adjustable in length.

The two slidably connected segments 302, 304 of flexible mesh 206 slide along each other to adjust an overall length of the fixation belt 102 in one embodiment. The two slidably connected segments 302, 304 may comprise a first segment 302 and a second segment 304. In one embodiment, the release 204 is connected to the second segment 304 and is releasably connected to the first segment 302. In an alternate embodiment, the release 204 is releasably connected to both the first segment 302 and the second segment 304.

In one embodiment, the release 204 includes a roller 306. The roller 306, in certain embodiments, is disposed at an interface between the two slidably connected segments 302, 304. In the illustrated embodiment, the roller 306 is disposed at an interface 310 with the first segment 302. The two slidably connected segments 302, 304 slide relative to one another in response to rolling of the roller 306 in certain embodiments.

In one embodiment, the fixation belt 102 includes a drive mechanism 308. The drive mechanism 308 causes the roller 306 to roll in response to actuation of the drive mechanism 308. In the illustrated embodiment, the drive mechanism 308 comprises a hex socket mated to the roller 306. The hex socket may be turned by a hex key or driver, causing the roller to turn. Beneficially, the drive mechanism 308 provides the practitioner with a means to install and tighten the fixation belt 102. In certain embodiments, the fixation belt 102 may be placed under tension by actuation of the drive mechanism 308.

Figure 4:
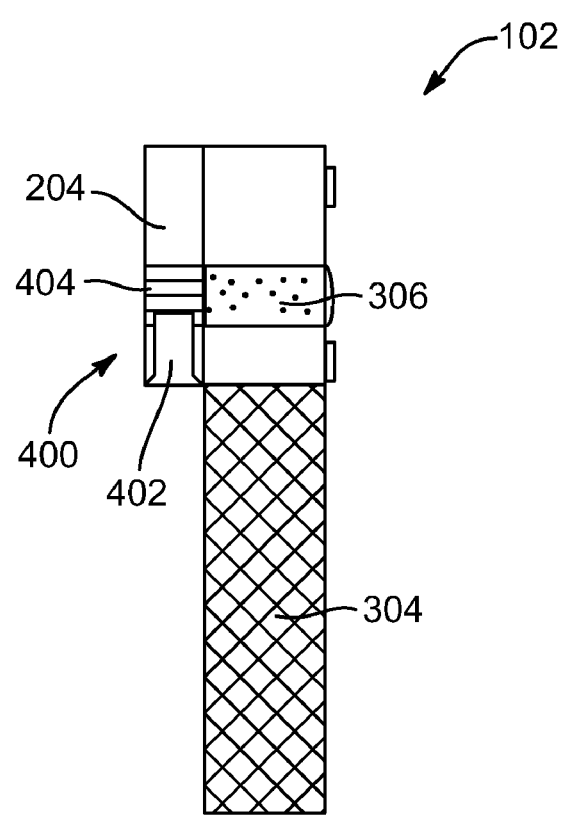
FIG. 4 is a front view further illustrating one embodiment of a fixation belt in accordance with the present invention.

FIG. 4 is a front view further illustrating the fixation belt 102 of FIG. 3 in accordance with the present invention, but with a ratchet mechanism 400 shown and the first segment 302 of the flexible mesh 206 removed. The second segment 302, the release 204, and the roller 306 are preferably configured in a similar manner to like-numbered components described in relation to FIG. 3. As shown, the roller 306 has a textured or high-frictioned surface configured to frictionally engage the first segment 302. The roller 306 is coupled to the ratchet mechanism 400 that includes a pawl 402 in ratcheting engagement with a ratcheting wheel 404.

Figure 5:
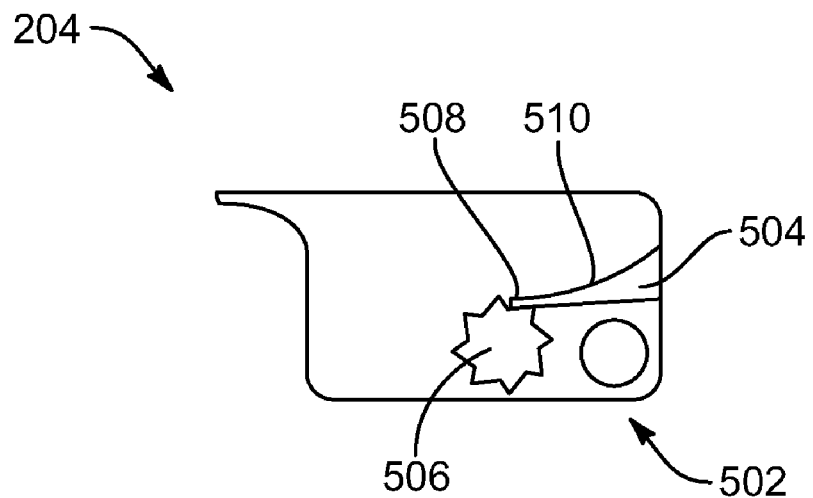
FIG. 5 is a side view further illustrating a release with a ratchet in accordance with the present invention.

FIG. 5 is a side view further illustrating a release 204 with a ratchet mechanism 502 similar to ratchet mechanism 400 disposed in the release 204 in accordance with the present invention. The ratchet mechanism 502, in the illustrated embodiment, includes a pawl 504 and a gear wheel 506. The ratchet mechanism 502 restricts the rotation of the roller 306 in one direction while allowing rotation of the roller 306 in the other direction.

The gear wheel 506, in one embodiment, is connected to the roller 306. In certain embodiments, rotation of the roller 306 results in rotation of the gear wheel 506. In one embodiment, a restriction of rotation of the gear wheel 506 causes a similar restriction of rotation of the roller 306.

In the illustrated embodiment, the gear wheel 506 comprises a plurality of teeth that engage with a pawl 504. As will be appreciated by one skilled in the art, a variety of other types and configurations of gear wheels may be employed without departing from the scope of the invention. For example, in one embodiment, the gear wheel 506 may comprise a high friction surface, such as a synthetic rubber, which engages with a pawl 504.

The pawl 504, in the illustrated embodiment, comprises an engagement surface 508 and a spring 510. The engagement surface 508 contacts the gear wheel 506 restricting rotation of the gear wheel 506 in one direction. In certain embodiments, the gear wheel 506 includes sloped teeth causing this one-way rotation as will be appreciated by one skilled in the art. In one embodiment, the pawl 504 is angled such that rotation of the gear wheel 506 in one direction causes the engagement surface 508 to interfere with the gear wheel 506 to restrict rotation.

The spring 510, in one embodiment, causes the engagement surface 508 of the pawl 504 to contact the gear wheel 506. In one embodiment, the spring 510 comprises a compliant element that drives the pawl 504 against the gear wheel 506. In the illustrated embodiment, the spring 510 comprises the pawl 504 itself, which elastically deforms and flexes to accommodate rotation of the gear wheel 506.

In one embodiment, the release 204 has a disengaged position. In certain embodiments, the engagement surface 508 is removed from the gear wheel 506 in response to the release 204 being in a disengaged position. Beneficially, the roller 306 is free to rotate in either direction in response to the release 204 being in the disengaged position, and the fixation belt 102 can thus be quickly removed. One embodiment of a disengaged position of a release 204 is described in relation to FIG. 9.

Figure 6:
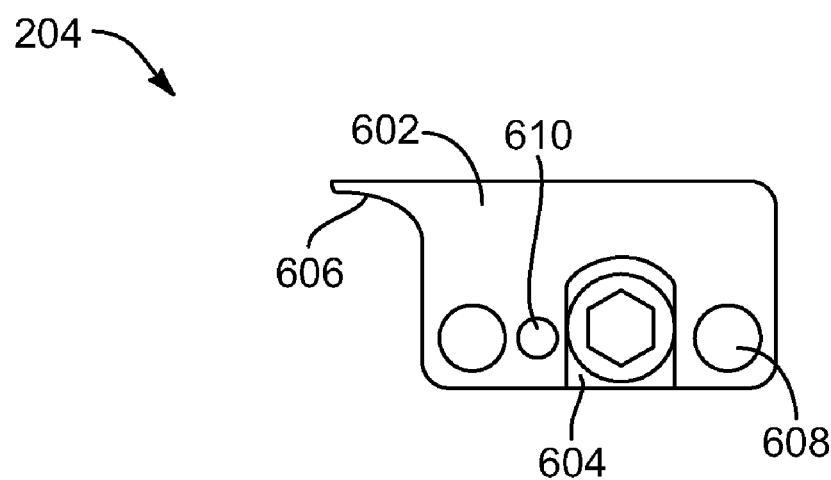
FIG. 6 is a side view further illustrating one embodiment of a release in accordance with the present invention.

FIG. 6 is a side view further illustrating one embodiment of a release 204 in accordance with the present invention. In one embodiment, the release 204 includes a gate 602, a body 604, a fingernail flange 606, a hinge 608, and a compliant snap 610. The release 204 is configured to release the fixation belt 206 for removal or adjustment.

In the illustrated embodiment, the gate 602 is shown in an engaged position relative to the body 604. The gate 602, in certain embodiments, rotates around the hinge 608 between the gate 602 and the body 604. In one embodiment, the gate 602 may rotate between an engaged position and a disengaged position.

In one embodiment, the gate 602 interacts with a pawl 504 to restrict the rotation of a gear wheel 506 in one direction in response to the gate 602 being in the engaged position. In another embodiment, the gate 602 interferes with one or both of the two slidably connected segments 302, 304 to restrict relative motion between the segments 302, 304 in response to the gate 602 being in the engaged position.

In one embodiment of the release 204, the gate 602 includes a fingernail flange 606. The fingernail flange 606 may comprise a protruding flange extending from the gate 602 that is accessible without tools by a fingernail. The fingernail flange 606, in the illustrated embodiment, is located distally from the hinge 608, allowing for greater leverage on the gate 602. Beneficially, the fingernail flange 606 allows a user to pivot the gate 602 around the hinge 608, placing the release 204 in a disengaged position and releasing the fixation belt 102 without the use of tools.

The compliant snap 610, in one embodiment, holds the gate 602 in an engaged position. In certain embodiments, the compliant snap 610 releases the gate 602 from the body 604 in response to pressure applied to the fingernail flange 606. In the illustrated embodiment, the compliant snap 610 comprises a protrusion in one of the gate 602 and the body 604 and a depression in the other of the gate 602 and the body 604. In this embodiment, the gate 602 and/or the body 604 flexes as force is applied to open the release 204, releasing the compliant snap 610.

As will be appreciated by one skilled in the art, a variety of types and configurations of compliant snap 610 may be employed without departing from the scope of the invention. For example, the compliant snap 610 may comprise a ridge disposed on the gate 602 configured to fit around the body 604.

Figure 7:
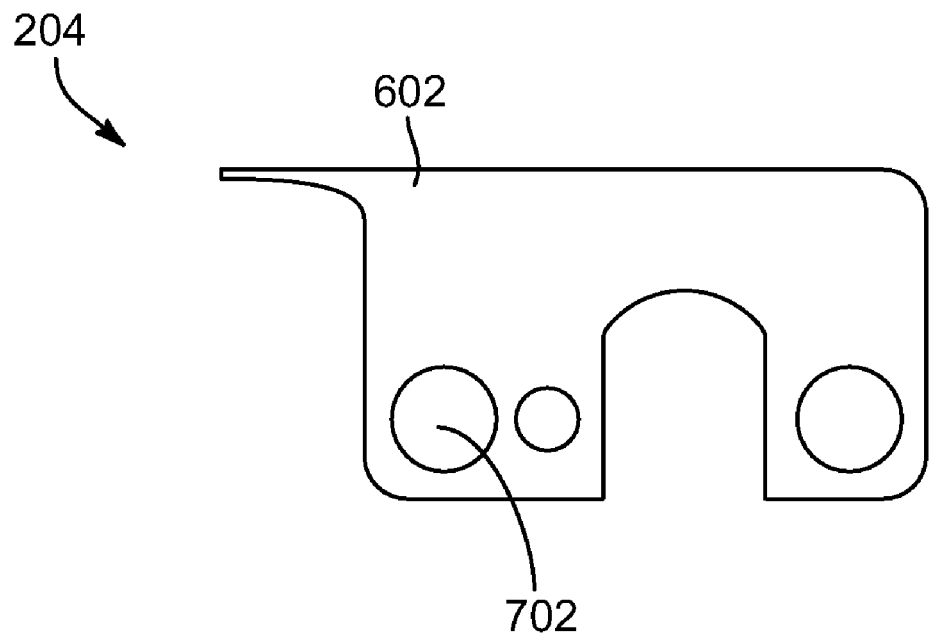
FIG. 7 is a side view illustrating a release with a compliant connection for an indicator plug in accordance with the present invention.

FIG. 7 is a side view illustrating a release 204 showing the gate only with a compliant connection 702 for an indicator plug in accordance with the present invention. The compliant connection 702 receives an indicator plug that interfaces with the body 604 and the gate 602. The indicator plug fractures in response to the gate 602 being moved to a disengaged position, and a fractured or missing indicator plug indicates that the fixation belt 102 has been released.

In one embodiment, the compliant connection 702 comprises mating circular apertures in the gate 602 and the body 604. In this embodiment, the indicator plug is pressed through the mating apertures of the compliant connection 702. The indicator plug may flex as it is pressed through the mating apertures. In an alternate embodiment, the compliant connection 702 flexes as the indicator plug is installed.

Figure 8:
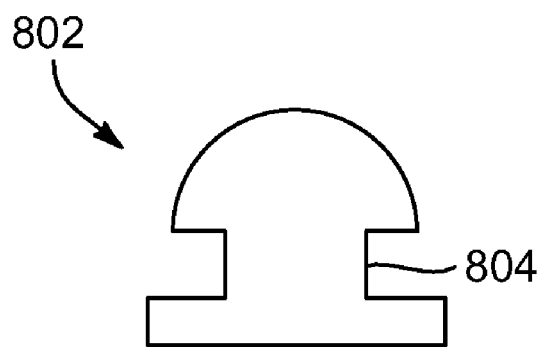
FIG. 8 is a front view of an indicator plug in accordance with the present invention.

FIG. 8 is a front view of one embodiment of an indicator plug 802 in accordance with the present invention. In the illustrated embodiment, the indicator plug 802 includes a fracture area 804. The indicator plug 802 connects to the release 204 and indicates by its presence that the fixation belt 102 has not been released.

In one embodiment, the fracture area 804 of the indicator plug 802 is a section of the indicator plug 802 that fractures in response to the release 204 being placed in a disengaged position. In the illustrated embodiment, when the indicator plug 802 is installed in the compliant connection 702, the fracture area 802 is located near an interface between the body 604 and the gate 602. In this embodiment, the indicator plug 802 is sheared apart at the fracture area 804 in response to the release 204 being moved to a disengaged position.

The indicator plug 802 may comprise any material rigid enough to be held in the compliant connection 702, flexible enough to be installed in the compliant connection 702, and fragile enough to fracture at the fracture area 804 in response to a pressure applied by a fingernail at the fingernail flange 606.

Figure 9:
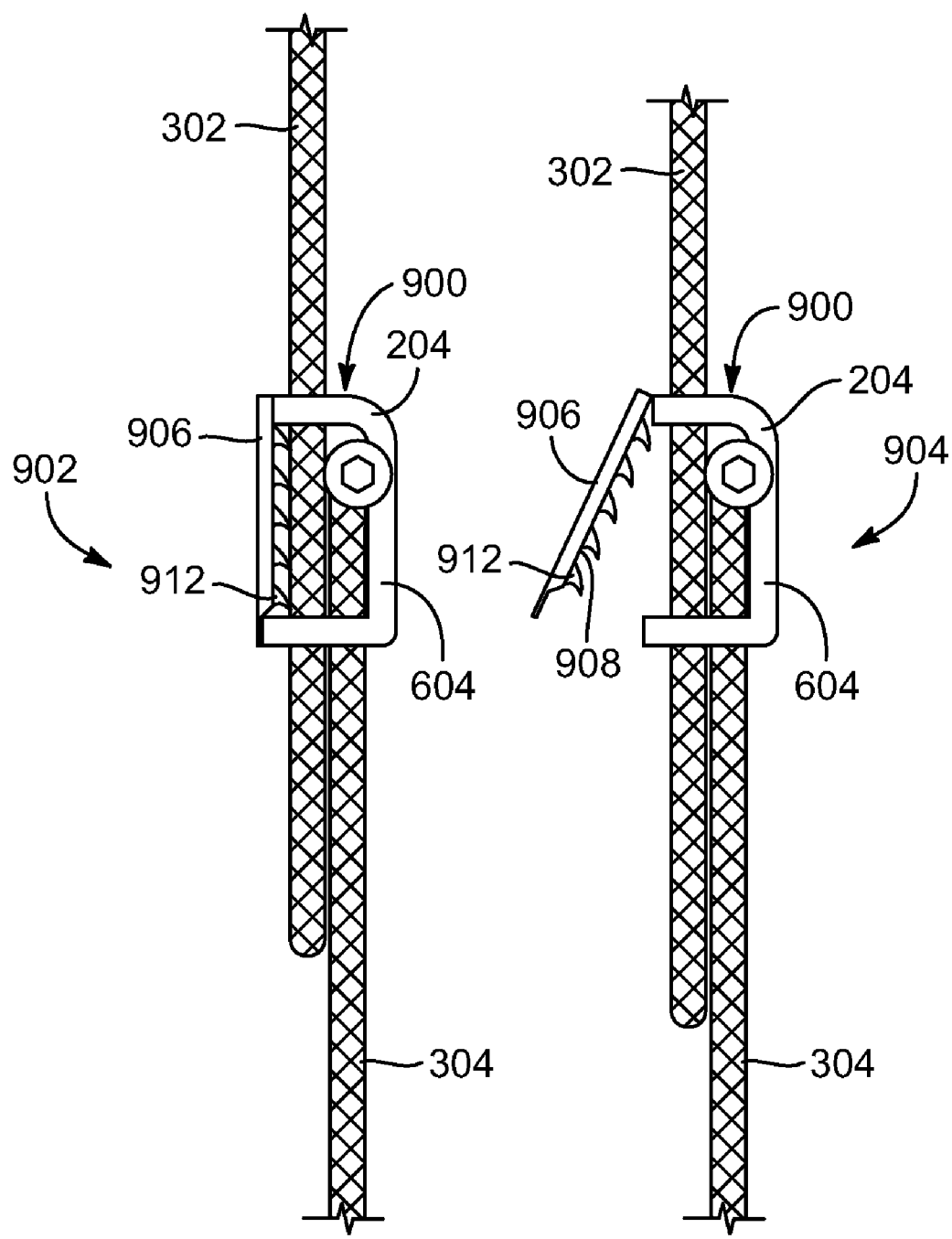
FIG. 9 is a side view of a release in an engaged position and a disengaged position.

FIG. 9 is a side view of an alternative embodiment of a release 900 in an engaged position 902 and a disengaged position 904. The release 900 includes a gate 906 and a body 904 in the illustrated embodiment. In the engaged position, the release 900 restricts movement between the plurality of fasteners 202 of the fixation belt 102. In the disengaged position 904, the release 900 allows movement between the plurality of fasteners 202 of the fixation belt 102.

In the embodiment shown in FIG. 9, the gate 906 has an interior surface 908 that interferes with one or more of the two slidably connected segments 302, 304 of the fixation belt 102 in response to the release being in the engaged position 902. For example, the interior surface 908 of the gate 906 may have one or more teeth 912 that extend into the flexible mesh 206 while the gate 906 is in the engaged position 902. In this embodiment, the interior surface 908 is removed from the two slidably connected segments 302, 304 in response to the release being moved to the disengaged position 904. In the above example, the one or more teeth 912 release the flexible mesh 206 in response to the interior surface 906 being removed from the two slidably connected segments 302, 304. Similar to the gate 906 and teeth 912, movement of the gate 602 in FIGS. 4 and 5 into the disengaged position correspondingly moves the pawl 504, which can be attached to the gate 602, such that it is released from a gear wheel 506.

Figure 10:
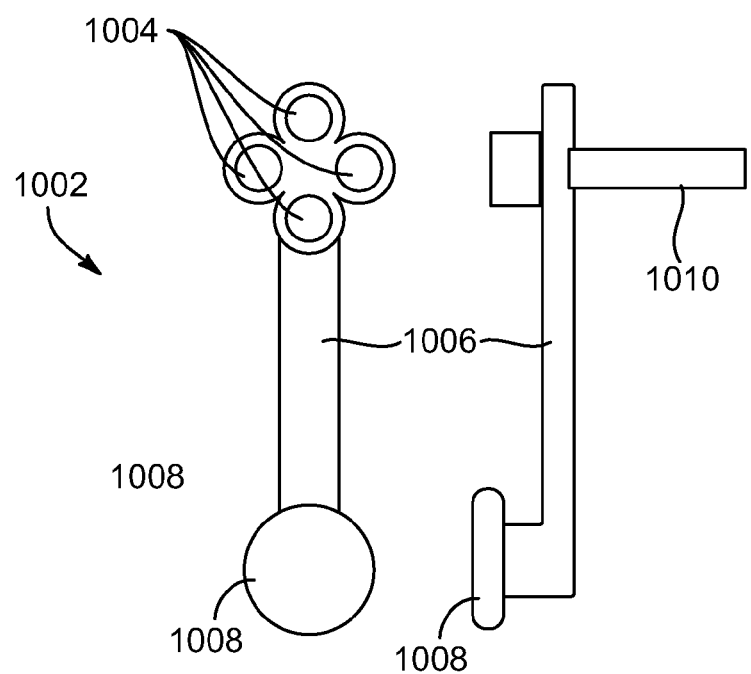
FIG. 10 is a front and side view of a connector in accordance with the present invention.

FIG. 10 is a front and side view of a connector 1002 in accordance with the present invention. In the illustrated embodiment, the connector 1002 includes one or more anchor attachments 1004, an extension arm 1006, and a fixation belt attachment 1008. The connector 1002 provides a connection for a fastener 202 of a fixation belt 102.

The one or more anchor attachments 1004, in one embodiment, attach to one or more anchors 1010 to fasten the connector 1002 to bone. The one or more anchors 1010 may comprise any anchor known in the art. For example, in the illustrated embodiment, the one or more anchor attachments 1004 comprise apertures in the connector 1002 and the one or more anchors 1010 comprise standard bone fixation screws passing through the apertures and into bone.

The one or more anchor attachments 1004 may be located in any position or configuration convenient for anchoring the connector 1002 to bone. For example, in the illustrated embodiment, the connector 1002 includes four anchor attachments 1004 arranged in a diamond pattern. This configuration provides a stable attachment when a large bone surface is available for anchoring the connector 1002. Some additional configurations of anchor attachments are described in relation to FIG. 11 below.

The extension arm 1006 separates the one or more anchor attachments 1004 from the fixation belt attachment 1008 in one embodiment. In certain circumstances, the most desirable location for anchoring the connector 1002 to bone is in a different location than the most desirable location for fastening the fixation belt 102. For example, in one embodiment, the one or more anchors 1010 are surgically implanted beneath tissue, but it is desirable to have the fixation belt attachment 1008 accessible for adjustment, replacement, or emergency removal. In this example, by providing an extension arm 1006, the one or more anchors 1010 may be located beneath tissue while the fixation belt attachment 1008 remains accessible.

In another example, a trauma patient may not have stable bone accessible in the lower part of the mandible. In this example, a relatively long extension arm 1006 allows the connector 1002 to be anchored relatively high in the mandible while locating the fixation belt attachment 1008 at the optimal position. Connectors 1002 with a variety of lengths, configurations, and angles of extension arm 1006 may be made available to accommodate diverse circumstances and needs.

The fixation belt attachment 1008, in one embodiment, interfaces with the fastener 202 of a fixation belt 102 to fasten the fixation belt 102 to the connector 1008. The fixation belt attachment 1008 may comprise any type of fastener known in the art. In the illustrated embodiment, the fixation belt attachment 1008 comprises a button over which a keyhole fastener 202 is placed as described in relation to FIG. 2. Alternate embodiments of the fixation belt attachment 1008 include, but are not limited to, a hook, a catch, a clasp, a snap, or other fasteners. In one embodiment, the fixation belt attachment 1008 may comprise keyhole fastener and the fastener 202 may comprise a button that seats in the keyhole fastener.

Figure 11:
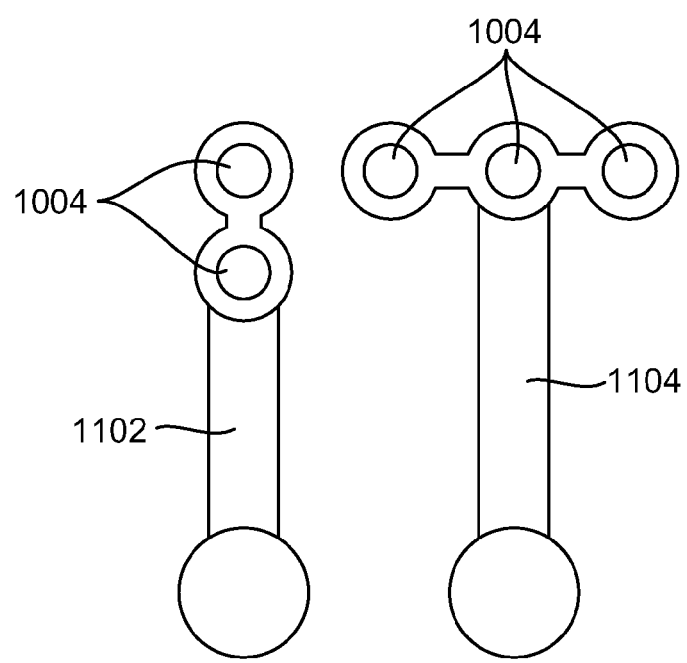
FIG. 11 is a front view illustrating alternate embodiments of anchor attachments for connectors in accordance with the present invention.

FIG. 11 is a front view illustrating alternate embodiments of one or more anchor attachments 1004 for connectors 1002 in accordance with the present invention. As described above in relation to FIG. 10, the one or more anchor attachments 1004 may comprise any combination or arrangement of attachments that may meet differing needs. The illustrated embodiments include a connector 1102 with two anchor attachments 1004 arranged along the length of the connector 1102, and a connector 1104 with three anchor attachments 1004 arranged perpendicular to the length of the connector 1104.

Figure 12:
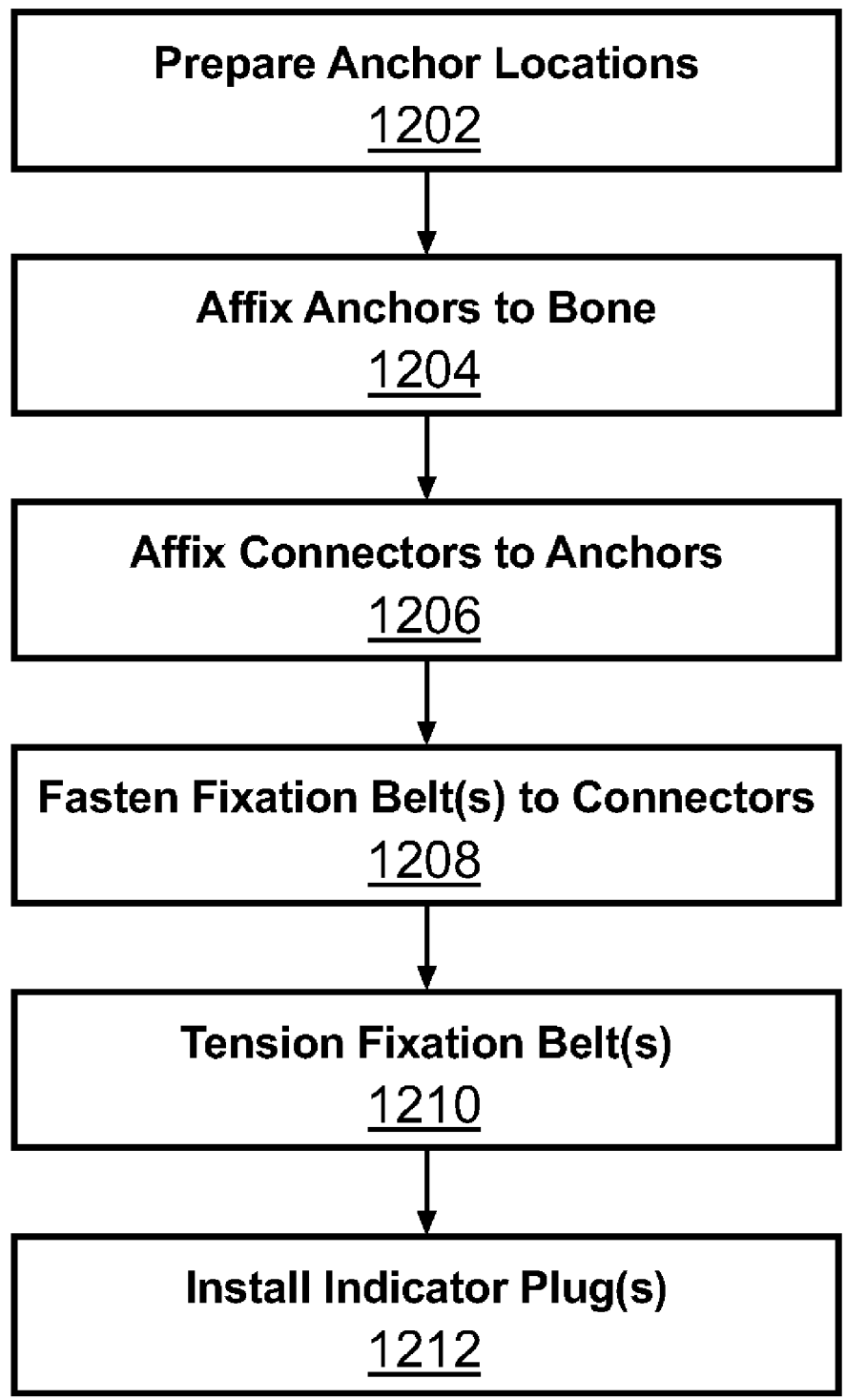
FIG. 12 is a flow chart diagram illustrating a method for maxillo-mandibular fixation in accordance with the present invention.

FIG. 12 is a flow chart diagram illustrating the various steps in a method 1200 for maxillo-mandibular fixation in accordance with the present invention. The method 1200 is in certain embodiments a method of use of the system and apparatus of FIGS. 1-11, and will be discussed with reference to those figures. Nevertheless, the method 1200 may also be conducted independently thereof and is not intended to be limited specifically to the specific embodiments discussed above with respect to those figures.

As shown in FIG. 12, in the prepare anchor locations step 1202, locations on the patient are prepared 1202 to receive anchors 1010. Preparing anchor locations 1202 may comprise surgically exposing bone tissue in one embodiment.

In the affix anchors to bone step 1204, anchors 1010 are affixed 1204 to bone tissue. In one embodiment, the anchors 1010 may comprise bone fixation screws, and the anchors 1010 may be affixed 1204 using a drive tool. For example, the anchors 1010 may have a hex head, and the anchors 1010 may be affixed 1204 using a hex drive tool.

In the affix connectors to anchors step 1206, one or more connectors 1002 are affixed 1206 to one or more anchors 1010. In one embodiment, the anchors 1010 comprise screws and the connectors 1010 are affixed 1206 to the anchors 1010 by passing the screws through anchor attachments 1004 as the anchors are affixed 1204 to bone. In an alternate embodiment, one or more connectors 108 may be affixed 1206 to anchors 1010 using any fastening method known in the art, such as a snap, a hook, a clasp, or the like.

In the fasten fixation belt(s) to connectors step 1208, one or more fixation belts 102 are fastened 1208 to a plurality of connectors 1002. As described above, the one or more fixation belts 102 may be fastened 1208 using fasteners 202 and fixation belt attachments 1008.

In the tension fixation belt(s) step 1210, the one or more fixation belts 102 are tensioned 1210 to hold the maxilla 104 and mandible 106 in position relative to one another. In one embodiment, the one or more fixation belts 102 are tensioned using a drive mechanism 308.

In the install indicator plug(s) step 1212, one or more indicator plugs 802 are installed 1212 into the releases 204 of the one or more fixation belts 102. In one embodiment, the one or more indicator plugs 802 are installed 1212 into compliant connections 702 on the releases 204.

Referring to FIG. 13, an alternative embodiment of a portion of a fixation belt 1300 in accordance with the present invention is shown. The fixation belt 1300, in one embodiment, includes two slidably connected segments 302, 304, a release 1302, a drive mechanism 1304, and quick release 1306. The fixation belt 102 in the illustrated embodiment is adjustable in length.

The two slidably connected segments 302, 304 slide along each other to adjust an overall length of the fixation belt 1300 in one embodiment. The two slidably connected segments 302, 304 may comprise a first segment 302 and a second segment 304. In one embodiment, the release 1302 is connected to the first segment 302 and is releasably connected to the second segment 304. In an alternate embodiment, the release 1302 is releasably connected to both the first segment 302 and the second segment 304.

In the illustrated embodiment, the second segment 304 of the fixation belt 1300 includes a toothed region 1308. The toothed region 1308 engages the release such that relative movement between the two slidably connected segments 302, 304 is restricted. In one embodiment, the toothed region 1308 restricts relative movement between the two slidably connected segments 302, 304 that increases the overall length of the fixation belt 1300 while allowing movement that decreases the overall length of the fixation belt 1300.

In one embodiment, the drive mechanism 1304 is disposed at an interface between the two slidably connected segments 302, 304. The drive mechanism 1304 is configured to articulate in response to a movement of the two slidably connected segments 302, 304 relative to one another that decreases the overall length of the fixation belt 1300 in certain embodiments. The drive mechanism 1304, when actuated, causes the two slidably connected segments 302, 304 to move relative to one another such that the overall length of the fixation belt 1300 is shortened.

Figure 14:
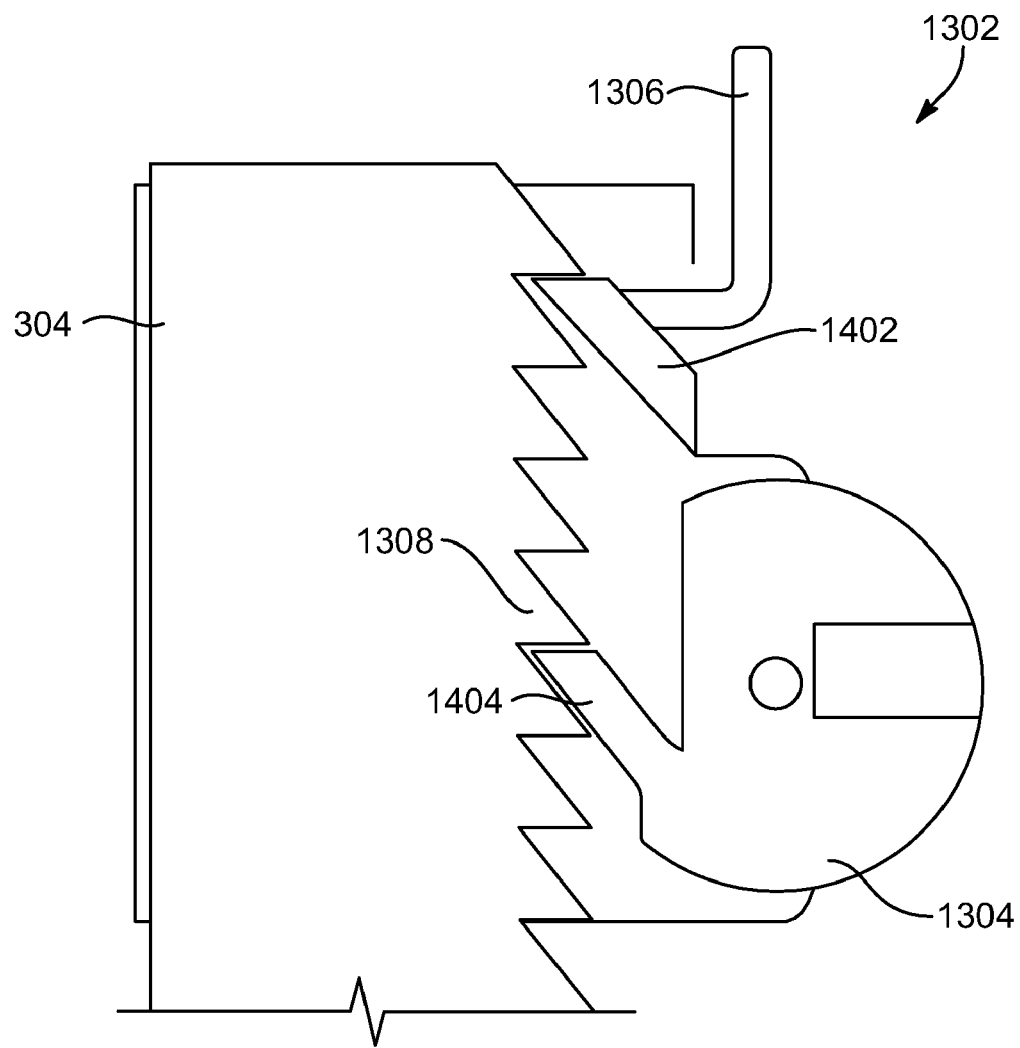
FIG. 14 illustrates a front view of a release engaging a second segment of the fixation belt of FIG. 13A shown with a front panel removed from the release.

Referring to FIG. 14, the release 1302 is shown engaging the second segment 304 of the fixation belt 1300 of FIG. 13A. As discussed above, the release 1302 engages the second segment 304 of the fixation belt 1300.

The quick release or catch 1306 directly engages the second segment 304 of the fixation belt. In certain embodiments, the catch 1306 includes a pawl 1402 that engages the toothed region 1308 of the second segment 304. The toothed region 1308 may interact with the pawl 1402 of the catch 1306 such that the second segment 304 is restricted from moving in a direction that increases the overall length of the fixation belt 1300.

The catch 1306 may be actuated to move the pawl 1402 away from the toothed region 1308 to release the second segment 304. In other words, the pawl 1402 of the catch 1306 is removed from the toothed region 1308 of the second segment 304 in response to actuation of the catch 1306.

The drive mechanism 1304, in one embodiment, is actuated by rotation of the drive mechanism. In certain embodiments, the drive mechanism 1304 includes a drive pawl 1404 that engages the toothed region 1308 of the second segment 304. The drive pawl 1404 and the toothed region 1308, in the illustrated embodiment, have a sloped interaction surface that allows the drive mechanism 1304 to ratchet, causing the overall length of the fixation belt 1300 to decrease. For example, the drive mechanism 1304 may be rotated several times, causing the drive pawl 1404 and the toothed region 1308 to ratchet, shortening the fixation belt 1300, and therefore tightening the connection between the maxilla and mandible.

Figure 15A:
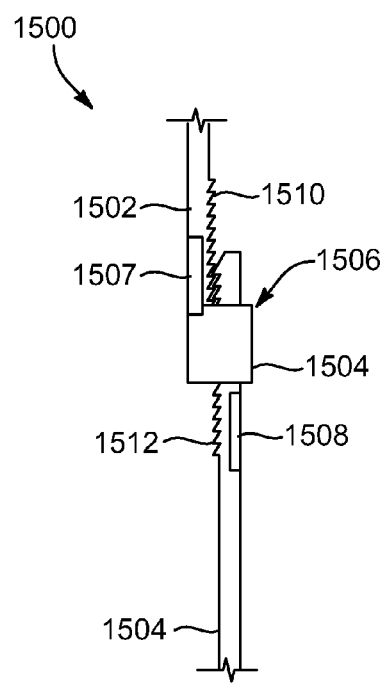
FIG. 15A is a side elevation view illustrating an alternative embodiment of a portion of a fixation belt in accordance with the present invention.

Referring to FIG. 15A, a portion of a fixation belt 1500 in accordance with the present invention is shown. The fixation belt 1500, in the illustrated embodiment, includes a first segment 1502, a second segment 1504, and a release 1506. The fixation belt 1500 secures a maxilla to a mandible.

In the illustrated embodiment, the first segment 1502 includes a toothed region 1510. The toothed region 1510 may include sloped teeth that create a higher resistance to sliding in one direction along the axis of the first segment 1502 and a lower resistance to sliding in the other direction along the axis of the first segment 1502 similar to teeth 912.

The second segment 1504, in the illustrated embodiment, also includes a toothed region 1512. The toothed region 1512 may include sloped teeth that create a higher resistance to sliding in one direction along the axis of the second segment 1504 and a lower resistance to sliding in the other direction along the axis of the first segment 1504.

In one embodiment, the teeth of the toothed regions 1510, 1512 interact to allow the first segment 1502 to slide along the second segment 1504 in a manner that causes the overall length of the fixation belt 1500 to decrease. In the illustrated embodiment, the teeth of the toothed regions 1510, 1512 also engage to restrict movement that causes the overall length of the fixation belt 1500 to increase.

The first segment 1502, in one embodiment, also includes a binder 1504. The binder 1504 guides the second segment 1504 as it slides along the first segment 1502 in the illustrated embodiment. The binder 1504 may cause the teeth of the toothed regions 1510, 1512 to engage.

Figure 15B:
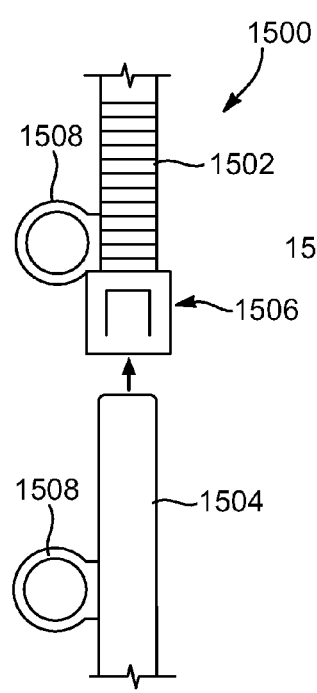
FIG. 15B is a front elevation view of the portion of a fixation belt of FIG. 15A.
Figure 15C:
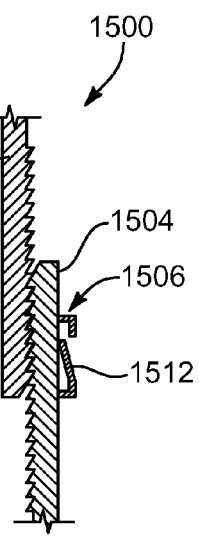
FIG. 15C is a cross-sectional side elevation view of the portion of a fixation belt of FIG. 15A showing a retention spring.

Referring to FIG. 15C, in one embodiment, the binder 1504 includes a spring 1512. The spring 1512, in the illustrated embodiment, exerts a force that causes the first segment 1502 to engage the second segment 1504. In certain embodiments, the spring 1512 is compliant, and flexes in response to a movement between the first segment 1502 and the second segment 1504 that causes the overall length of the fixation belt 1500 to decrease.

Referring to FIG. 15B, in certain embodiments, the first segment 1502 includes a drive socket 1508. In some embodiments, the second segment 1504 also includes a drive socket 1508. The drive sockets 1508 receives a tool (not shown) that causes the first segment 1502 to slide along the second segment 1504 such that the overall length of the fixation belt 1500 is decreased.

Figure 16A:
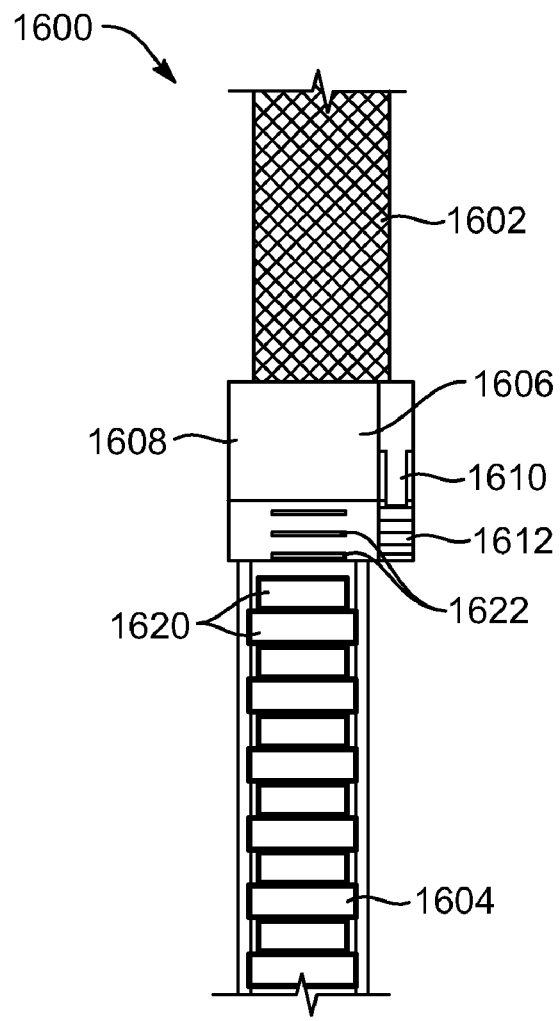
FIG. 16 is a front and side view illustrating an alternative embodiment of a portion of a fixation belt in accordance with the present invention.
Figure 16B:
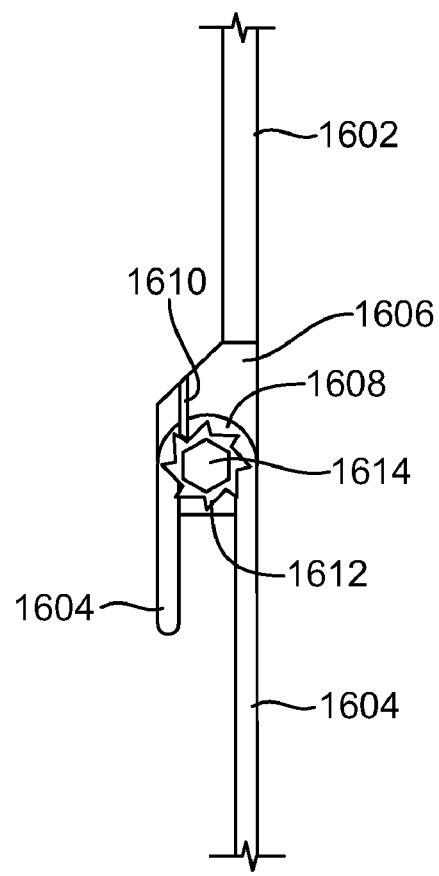

FIGS. 16A and 16B show an alternative embodiment of a portion of a fixation belt 1600 in accordance with the present invention. The fixation belt 1600, in the illustrated embodiment, includes a first segment 1602, a second segment 1604 and a release 1606. The fixation belt 1600 secures a maxilla to a mandible.

In one embodiment, the first segment 1602 is a flexible mesh. The flexible mesh of the first segment 1602 is elastically deformable under the forces used for securing a maxilla to a mandible. While under elastic deformation, the first segment 1602 provides a force holding the maxilla and mandible together.

The second segment 1604, in certain embodiments, is a chain that does not undergo appreciable elastic deformation under the forces used to secure the maxilla to the mandible. The second segment 1604 may engage a roller 1608 in the release 1606. In certain embodiments, apertures 1620 in the second segment 1604 engage teeth 1622 on the roller 1608.

As will be appreciated by one skilled in the art, either segment 1602, 1604 may have at least some elastic deformation under the forces used to secure the maxilla to the mandible. For example, both the first segment 1602 in the second segment 1604 may be elastically deformable. In another example, the second segment 1604 may be elastically deformable, while the first segment 1602 does not undergo appreciable elastic deformation under the forces used to secure the maxilla to the mandible.

The release 1606, in one embodiment, also includes a catch 1610, a ratchet wheel 1612, and a drive mechanism 1614. The release 1606 is disposed at an interface between the first segment 1602 and the second segment 1604 in one embodiment. In the illustrated embodiment, the release 1606 connects the first segment 1602 to the second segment 1604 and manages the overall length of the fixation belt 1600.

The roller 1608, in one embodiment, engages the second segment 1604. In the illustrated embodiment, the second segment 1604 moves in relation to the first segment 1602 in response to a rotation of the roller 1608. As discussed above, in one embodiment, the roller 1608 includes one or more teeth 1622 that engage the second segment 1604. Referring to FIG. 16B, the teeth 1622 facilitate engagement of the second segment 1604 to the roller to allow the second segment to be rolled about the roller 1608 as the ratchet wheel 1612 is turned. As shown, in certain embodiments, a leading portion of the second segment 160 can hang from the roller 1608 after being released from engagement with the roller.

In certain embodiments, the release 1606 includes a catch 1610. The catch 1610, in one embodiment, restricts the rotation of the roller 1608. In the illustrated embodiment, the catch 1610 engages the ratchet wheel 1612 such that rotation of the roller 1608 is allowed in one direction and restricted in the other, such that the overall length of the fixation belt 102 may be decreased without disengaging the catch 1610. In certain embodiments, the overall length of the fixation belt 1600 may be increased by releasing the catch 1610.

The drive mechanism 1614, in one embodiment, is connected to the roller 1608 and causes the roller 1608 to rotate in response to rotation of the drive mechanism 1614. In the illustrated embodiment, the drive mechanism 1614 is a hex socket. The hex socket may be engaged by a hex wrench to rotate the roller 1608, move the second segment 1604, and decrease the overall length of the fixation belt 1600.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for maxillo-mandibular fixation, the apparatus comprising:
   a plurality of connectors comprising:
      one or more anchors configured to attach to bone; and
      a fixation belt attachment;
   a fixation belt comprising:
      a plurality of fasteners, each fastener attachable to a fixation belt attachment; and
      a flexible mesh disposed between the plurality of fasteners; and
   a release disposed on the fixation belt, the release having an engaged position restricting movement between the plurality of fasteners, and a disengaged position allowing movement between the plurality of fasteners.

2. The apparatus of claim 1 wherein the flexible mesh comprises a material selected from the group consisting of stainless steel, titanium, and a polymer.

3. The apparatus of claim 1 wherein the flexible mesh comprises two slidably connected segments.

4. The apparatus of claim 3 wherein:
   the release is disposed at an interface between the two slidably connected segments;
   the engaged position of the release restricts movement between the two slidably connected segments; and
   the disengaged position of the release allows movement between the two slidably connected segments.

5. The apparatus of claim 4 further comprising a ratchet disposed in the release, the ratchet comprising:
   a roller interfacing with each of the two slidably connected segments, rotation of the roller causing relative movement between the two slidably connected segments;
   a gear wheel connected to the roller; and
   a pawl comprising:
      a spring driving the pawl against the gear wheel; and
      an engagement surface contacting the gear wheel and restricting the rotation of the roller in one direction.

6. The apparatus of claim 5 further comprising a drive mechanism connected to the roller such that rotation of the drive mechanism rotates the roller.

7. The apparatus of claim 6 wherein the drive mechanism comprises a hex socket.

8. The apparatus of claim 5 wherein the engagement surface is removed from the gear wheel in response to the release being placed in the disengaged position.

9. A system for maxillo-mandibular fixation, the system comprising:
- a plurality of anchors comprising a screw configured to attach to bone and a connector attachment;
- a plurality of connectors comprising:
  - one or more anchor attachments, each anchor attachment attachable to a connector attachment; and
  - a fixation belt attachment;
- a fixation belt comprising:
  - a plurality of fasteners, each fastener attachable to a fixation belt attachment;
  - two slidably connected segments of flexible mesh disposed between the plurality of fasteners; and
- a release disposed on an interface between the two slidably connected segments of flexible mesh, the release being movable between an engaged position restricting movement between the two slidably connected segments of flexible mesh, and a disengaged position allowing movement between the two slidably connected segments of flexible mesh.

10. The system of claim 9, wherein the release further comprises a body and a gate, the gate connected to the body by a hinge, the gate movable between the engaged position and the disengaged position.

11. The system of claim 10 further comprising a fingernail flange on the gate.

12. The system of claim 10 further comprising a compliant snap disposed between the gate and the body, the compliant snap releasably holding the gate in the engaged position.

13. The system of claim 10 further comprising an indicator plug with a fracture area, the indicator plug interfering with movement of the gate from the engaged position to the disengaged position, the indicator plug allowing movement of the gate from the engaged position to the disengaged position in response to a fracture of the indicator plug at the fracture area.

14. The system of claim 13 wherein the indicator plug further comprises a compliant connection with the body of the release.

15. The system of claim 10 further comprising a ratchet disposed in the body of the release, the ratchet comprising:
- a roller interfacing with each of the two slidably connected segments, rotation of the roller causing relative movement between the two slidably connected segments;
- a gear wheel connected to the roller; and
- a pawl comprising:
  - a spring driving the pawl against the gear wheel; and
  - an engagement surface contacting the gear wheel and restricting the rotation of the roller in one direction.

16. The system of claim 15 wherein the spring driving the pawl against the gear wheel is released in response to the gate being in the disengaged position.

17. The system of claim 10 wherein the gate further comprises an interference surface, the interference surface interfering with the interface between the two slidably connected segments of flexible mesh and restricting movement between the two slidably connected segments of flexible mesh in response to the gate being in the engaged position.

18. The system of claim 9, wherein each of the plurality of connectors further comprise an extension arm disposed between the one or more anchor attachments and the fixation belt attachment.

19. An apparatus for maxillo-mandibular fixation, the apparatus comprising:
- a plurality of connectors comprising:
  - one or more anchors configured to attach to bone; and
  - a fixation belt attachment;
- a fixation belt comprising:
  - a plurality of fasteners, each fastener attachable to a fixation belt attachment; and
  - two slidably connected segments of flexible mesh disposed between the plurality of fasteners; and
- a release disposed on an interface between the two slidably connected segments of flexible mesh, the release having an engaged position restricting movement between the two slidably connected segments of flexible mesh, and a disengaged position allowing movement between the two slidably connected segments of flexible mesh;
- a ratchet disposed in the release comprising:
  - a roller interfacing with each of the two slidably connected segments, rotation of the roller causing relative movement between the two slidably connected segments;
  - a gear wheel connected to the roller; and
  - a pawl comprising a spring driving the pawl against the gear wheel, and an engagement surface contacting the gear wheel and restricting the rotation of the roller in one direction.

20. The apparatus of claim 19 wherein the pawl is freed from the gear wheel in response to the release being placed in the disengaged position.

21. A method for maxillo-mandibular fixation of a patient, the method comprising:
- fixing a plurality of anchors to at least one bone of the patient;
- coupling each of a plurality of connectors to a respective one of the plurality of anchors;
- coupling a first flexible fixation belt to a first of the plurality of connectors;
- coupling a second flexible fixation belt to a second of the plurality of connectors;
- releasably coupling the first flexible fixation belt to the second flexible fixation belt at a location between the first and second connectors; and
- tensioning the first and second flexible fixation belts relative to each other.

22. The method of claim 21, wherein the first and second flexible fixation belts are releasably coupled via a release mechanism, the method comprising actuating the release mechanism to reduce tension in the first and second flexible fixation belts.

23. The method of claim 22, further comprising coupling at least one indicator plug to at least one of the first and second flexible fixation belts, the at least one indicator plug configured to provide a visual indication that the release mechanism has been released.

* * * * *

UNITED STATES PATENT AND TRADEMARK OFFICE
CERTIFICATE OF CORRECTION

PATENT NO. : 8,062,032 B2  
APPLICATION NO. : 12/257013  
DATED : November 22, 2011  
INVENTOR(S) : Scott E. Bulloch et al.

Page 1 of 1

It is certified that error appears in the above-identified patent and that said Letters Patent is hereby corrected as shown below:

Column 3, Line 33

"the paw is freed"--- should read "the pawl is freed"

Signed and Sealed this  
Twenty-fourth Day of January, 2012

David J. Kappos  
*Director of the United States Patent and Trademark Office*